United States Patent
Zewge et al.

(10) Patent No.: US 10,550,385 B2
(45) Date of Patent: Feb. 4, 2020

(54) POST-SYNTHETIC ORTHOGONAL AMIDATION PLUS METAL CATALYZED AZIDE-ALKYNE CYCLOADDITION CLICK CHEMISTRY ON SIRNA

(71) Applicant: SIRNA THERAPEUTICS, INC., Cambridge, MA (US)

(72) Inventors: Daniel Zewge, Rahway, NJ (US); Gregory T. Copeland, Claremont, CA (US); Zhen Li, Westfield, NJ (US); Joseph D. Armstrong, Rahway, NJ (US)

(73) Assignee: SIRNA THERAPEUTICS, INC., Cambridge, MA (US)

(*) Notice: Subject to any disclaimer, the term of this patent is extended or adjusted under 35 U.S.C. 154(b) by 90 days.

(21) Appl. No.: 14/652,359

(22) PCT Filed: Dec. 18, 2013

(86) PCT No.: PCT/US2013/075914
§ 371 (c)(1),
(2) Date: Jun. 15, 2015

(87) PCT Pub. No.: WO2014/100069
PCT Pub. Date: Jun. 26, 2014

(65) Prior Publication Data
US 2015/0322433 A1 Nov. 12, 2015

Related U.S. Application Data

(60) Provisional application No. 61/740,083, filed on Dec. 20, 2012.

(51) Int. Cl.
| | | |
|---|---|---|
| *A61K 31/712* | (2006.01) | |
| *C12N 15/113* | (2010.01) | |
| *C07H 21/02* | (2006.01) | |
| *C12N 15/11* | (2006.01) | |

(52) U.S. Cl.
CPC .......... *C12N 15/113* (2013.01); *A61K 31/712* (2013.01); *C07H 21/02* (2013.01); *C12N 15/111* (2013.01); *C12N 2310/14* (2013.01); *C12N 2310/317* (2013.01); *C12N 2310/321* (2013.01); *C12N 2310/322* (2013.01); *C12N 2310/332* (2013.01); *C12N 2330/30* (2013.01)

(58) Field of Classification Search
CPC ...... A61K 31/713; C07H 21/02; C07H 21/00; C07H 19/056; C12N 15/113; C12N 15/111; C12N 2310/322; C12N 2310/332; C12N 2310/317; C12N 2310/321; C12N 2310/14; C12N 2330/30
USPC ............ 435/6.1, 6.11, 91.31, 91.1; 536/23.1, 536/24.5
See application file for complete search history.

(56) References Cited

U.S. PATENT DOCUMENTS

| | | | |
|---|---|---|---|
| 5,532,147 A | 7/1996 | Nilsson | |
| 6,147,200 A | 11/2000 | Manoharan et al. | |
| 8,114,636 B2* | 2/2012 | Agnew | C07D 207/40 422/422 |
| 8,541,569 B2* | 9/2013 | Srivastava | C07H 19/067 536/25.3 |
| 8,962,580 B2* | 2/2015 | Manoharan | C07H 21/00 514/252.06 |
| 9,441,228 B2* | 9/2016 | Zewge | C07C 217/40 |
| 2011/0137010 A1 | 6/2011 | Srivastava et al. | |
| 2012/0035115 A1* | 2/2012 | Manoharan | C07H 21/00 514/20.9 |
| 2014/0315762 A1* | 10/2014 | Keefe | C40B 50/16 506/26 |
| 2016/0348109 A1* | 12/2016 | Zewge | C07C 217/40 |
| 2018/0037893 A1* | 2/2018 | Stanton | C12N 15/113 |

FOREIGN PATENT DOCUMENTS

| | | |
|---|---|---|
| WO | 2010101951 A1 | 9/2010 |
| WO | 2011090968 A1 | 7/2011 |

OTHER PUBLICATIONS

Prakash, T.P., et al., "2'-O-[2(Amino)-2-oxoethyl] Oligonucleotides," Organic Letters 5(4):403-406 (2003).
Watts, J.K., et al., "Chemically modified siRNA: tools and applications," Drug Discovery Today 13(19/20):842-855 (2008).
Iyer et al., "Sythesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)", J. Med. Chem., 43: 2266-2274 (2000).
Amblard et al., "The Cu(I)-catalyzed Huisgen azide-alkyne 1,3-dipolar cycloaddition reaction in nucleoside, nucleotide and oligonucleotide chemistry", Chem. Rev., 109(9): 4207-4220 (2009).

* cited by examiner

*Primary Examiner* — Jane J Zara
(74) *Attorney, Agent, or Firm* — Jeffrey N. Townes; Cozen O'Connor

(57) ABSTRACT

This invention relates to a process for introducing two or more 2'-modifications into an RNA, wherein the RNA has a 2'-O substituent containing an alkyl ester functional group on one or more ribose rings of a strand and a 2'-O substituent containing an alkyne functional groups on one or more ribose rings on the same strand. The process comprises a) adding an amine compound to the RNA to form amidation reactions with the alkyl ester functional groups; b) dissolving the modified RNA from step (a) in a solvent to form a solution; and c) adding an organic azide and a copper or ruthenium catalyst to the solution obtained in step (b) to form 2'-azide-alkyne cycloaddition reaction products with the alkyne functional groups.

19 Claims, 9 Drawing Sheets
Specification includes a Sequence Listing.

| Apo-Sequence 5'-3" | Snap positions | Click positions |
|---|---|---|
| D | 8,10,12,14,16 | 7,9,11,13,15 |

POST-SYNTHETIC ORTHOGONAL AMIDATION PLUS METAL CATALYZED AZIDE-ALKYNE CYCLOADDITION CLICK CHEMISTRY ON SIRNA

PRIORITY CLAIM

This application claims priority to PCT Application No. PCT/US2013/075914, filed Dec. 18, 2013, and U.S. Provisional Application No. 61/740,083, filed Dec. 20, 2012, both of which are herein incorporated by reference in their entirety.

BACKGROUND OF THE INVENTION

RNA interference (RNAi) is an evolutionarily conserved cellular mechanism of post-transcriptional gene silencing found in fungi, plants and animals that uses small RNA molecules to inhibit gene expression in a sequence-specific manner. The RNAi machinery can be harnessed to destruct any mRNA of a known sequence. This allows for suppression (knock-down) of any gene from which it was generated and consequently preventing the synthesis of the target protein. Smaller siRNA duplexes introduced exogenously were found to be equally effective triggers of RNAi (Zamore, P. D., Tuschl, T., Sharp, P. A., Bartel, D. P. *Cell* 2000, 101, 25-33). Synthetic RNA duplexes can be used to modulate therapeutically relevant biochemical pathways, including ones which are not accessible through traditional small molecule control.

Chemical modification of RNA duplexes leads to improved physical and biological properties such as nuclease stability (Damha et al., *Drug Discovery Today*, 2008, 13(19/20), 842-855), reduced immune stimulation (Sioud *TRENDS in Molecular Medicine*, 2006, 12(4), 167-176), enhanced binding (Koller, E. et al., *Nucl. Acids Res.*, 2006, 34, 4467-4476), enhanced lipophilic character to improve cellular uptake and delivery to the cytoplasm.

Since robust chemistry is a prerequisite for biological studies, development of efficient and reproducible methods for preparation of various oligonucleotide conjugates is of considerable importance (Harri Lönnberg, *Bioconjugate Chemistry*, 2009, 20, 1065-1094).

Chemically modified siRNA may be used as therapeutics to improve siRNA efficacy. In principle, chemically modified siRNA may be used to overcome efficacy related problems such as half-life in vivo, biodistribution and potency (Gaynor, J. W.; Campbell, B. J.; Cosstick, R. *Chem. Soc. Rev.*, 2010, 39, 4169-4184).

Chemical modifications of RNA have relied heavily on work-intensive, cumbersome, multi-step syntheses of structurally novel nucleoside analogues and their corresponding phosphoramidites prior to RNA assembly. In particular, a major emphasis has been placed on chemical modification of the 2'-position of nucleosides. A rigorous approach to structure-activity-relationship (SAR) studies of chemical modifications will obviously require synthesis and evaluation of all four canonical ribonucleosides [adenosine (A), cytidine (C), uridine (U), guanosine (G)]. Furthermore, some chemical modifications bear sensitive functional groups that may be incompatible with state-of-the-art automated synthesis of RNA as well as subsequent downstream cleavage-deprotection steps. These attributes have made chemical modification of RNA prior to synthesis rather low-throughput and limited in scope.

Post-synthetic chemical modifications of RNA have centered for the most part on simple conjugation chemistry. Conjugation has largely been performed on either the 3'- or the 5'-end of the RNA via alkylamine and disulfide linkers. These modifications have allowed conjugation of RNA to various compounds such as cholesterol, fatty acids, poly (ethylene)glycols, various delivery vehicles and targeting agents such as poly(amines), peptides, peptidomimetics, and carbohydrates.

As 2'-OH is not required for siRNA to enter the RNAi pathway (Chiu, Y-L.; Rana, J. M. RNA, 2003, 9, 1034-1048), the 2'-position of ribose ring in siRNA is a common target for chemical modifications.

Methods for forming azido-modified nucleic acid conjugates of reporter molecules, carrier molecules or solid support utilizing "click" chemistry are disclosed in US 2008/0050731.

Synthesis of modified RNA and DNA utilizing an alkyne handle on a base and subsequent "click chemistry" is disclosed in WO 2008/052775 and in CN 101550175. Chemical modification of siRNA at the 2'-position using "click" chemistry is disclosed in WO 2011/0990968.

Recent reviews regarding "click" chemistry and oligonucleotide synthesis are covered by Gramlich et al., *Angew. Chem. Int. Ed.*, 2008, 47, 8350-8358; Amblard et al., *Chem. Rev.*, 2009, 109, 4207-4220.

Sequential bis-conjugation of oligonucleotides using click-oxime and click-Husigen protocols was reported by Defrancq et al. JOC, 2010, 75, 3927-3930.

There remains a need for a post synthetic method for modifying RNA molecules that can provide one or more of the following benefits: 1) avoids complex, tedious multi-step syntheses of each desired modified ribonucleoside; 2) allows diverse chemical modifications using high-fidelity chemistry that is completely orthogonal to commonly used alkylamino, carboxylate and disulfide linker reactivities; 3) allows introduction of functional groups that are incompatible with modern automated solid-phase synthesis of RNA and subsequent cleavage-deprotection steps; 4) allows introduction of functional groups useful as targeting ligands; 5) enables high-throughput structure-activity relationship studies on chemically modified RNA in 96-well format; and 6) allows for an efficient orthogonal post-synthetic chemical modifications at multiple sites

SUMMARY OF THE INVENTION

In one embodiment, a process for introducing two or more 2'-modifications into an RNA, wherein the RNA has an ester functional group at the 2'-position of one or more ribose rings on a strand and an alkyne functional group at the 2'-position of one or more ribose rings on the same strand, comprises: a) adding an amine to the RNA to form amides via amidation reactions with the ester functional group; b) dissolving the modified RNA from step (a) in a solvent to form a solution; and c) adding an organic azide and a metal catalyst to the solution obtained in step (b) to form triazoles via 2'-azide-alkyne cycloaddition reactions with the alkyne functional groups.

BRIEF DESCRIPTION OF THE FIGURES

FIG. 3A shows the results using duplexes obtained from multi-snapped and multi-clicked Apo B passenger strand sequences A-C, and FIG. 3B shows the results using a duplex obtained from multi-snapped and multi-clicked Apo B passenger strand sequence D.

DETAILED DESCRIPTION OF THE INVENTION

Figure 1A:
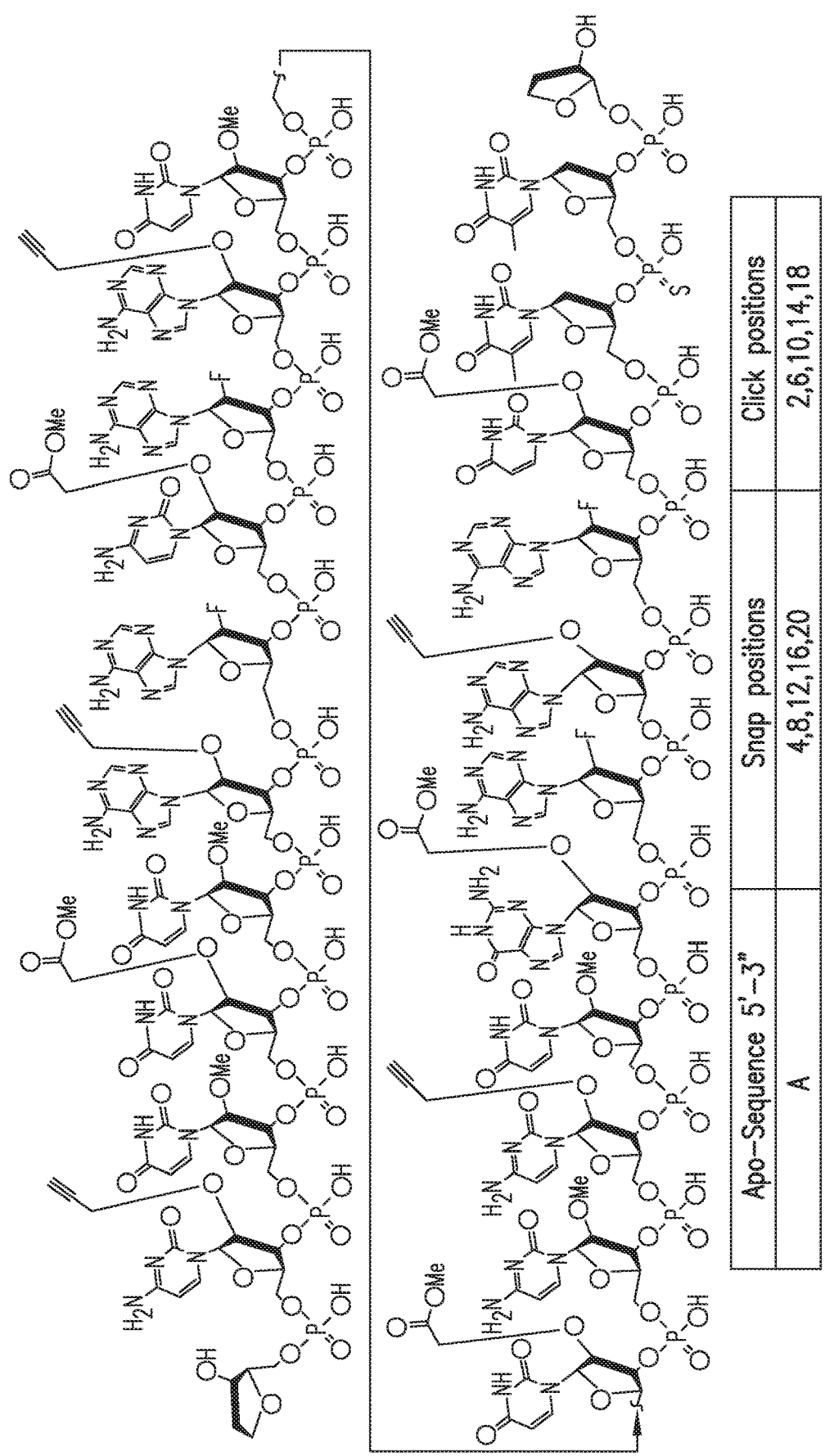
FIGS. 1A-1D show the structures of four siRNA (Apo B) passenger strands A-D (in FIG. 1A, FIG. 1B, FIG. 1C, and FIG. 1D, respectively) that can be used for multi-snap and multi-click modifications at different positions (positions indicated in table).
Figure 1B:
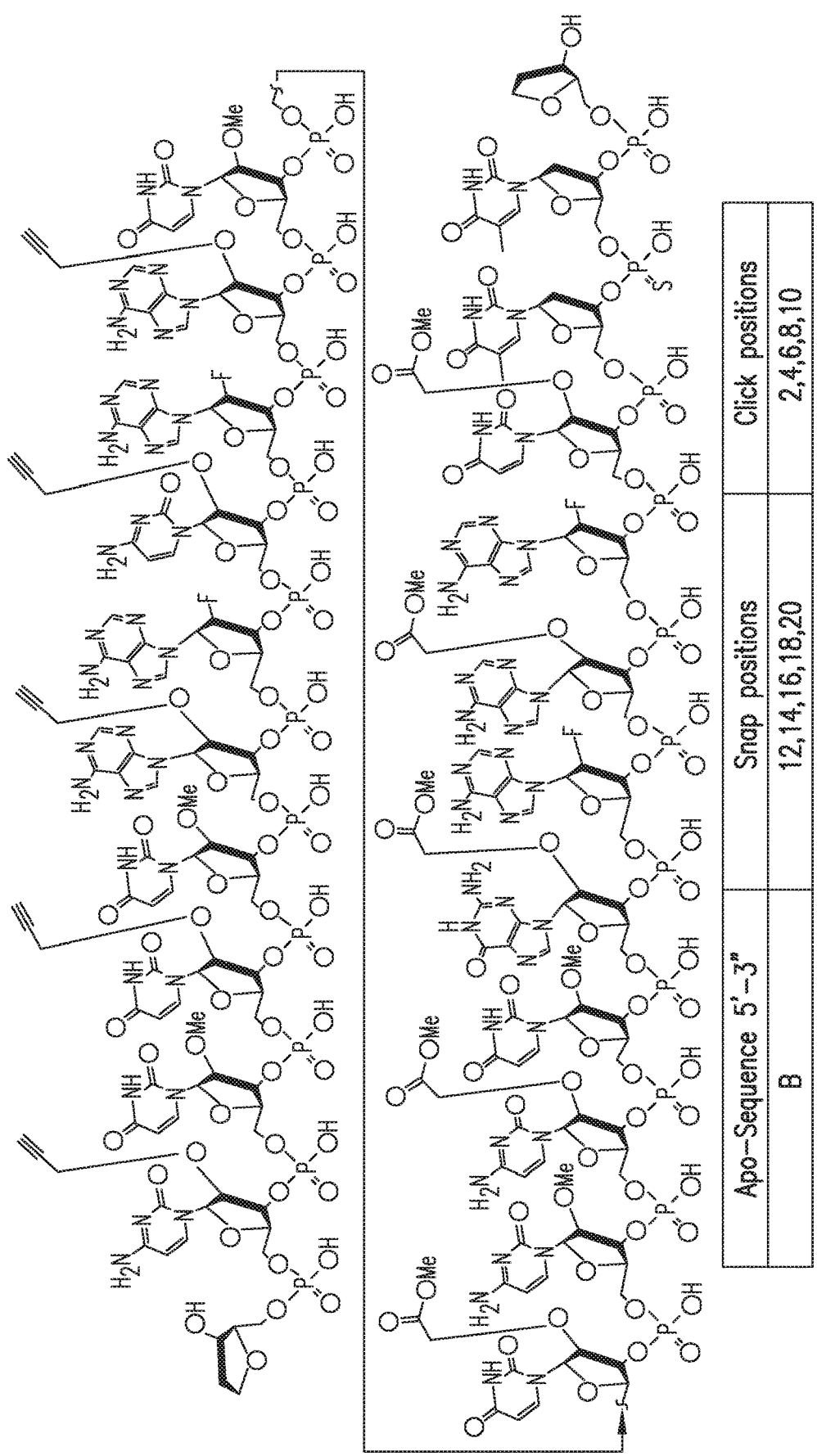
Figure 1C:
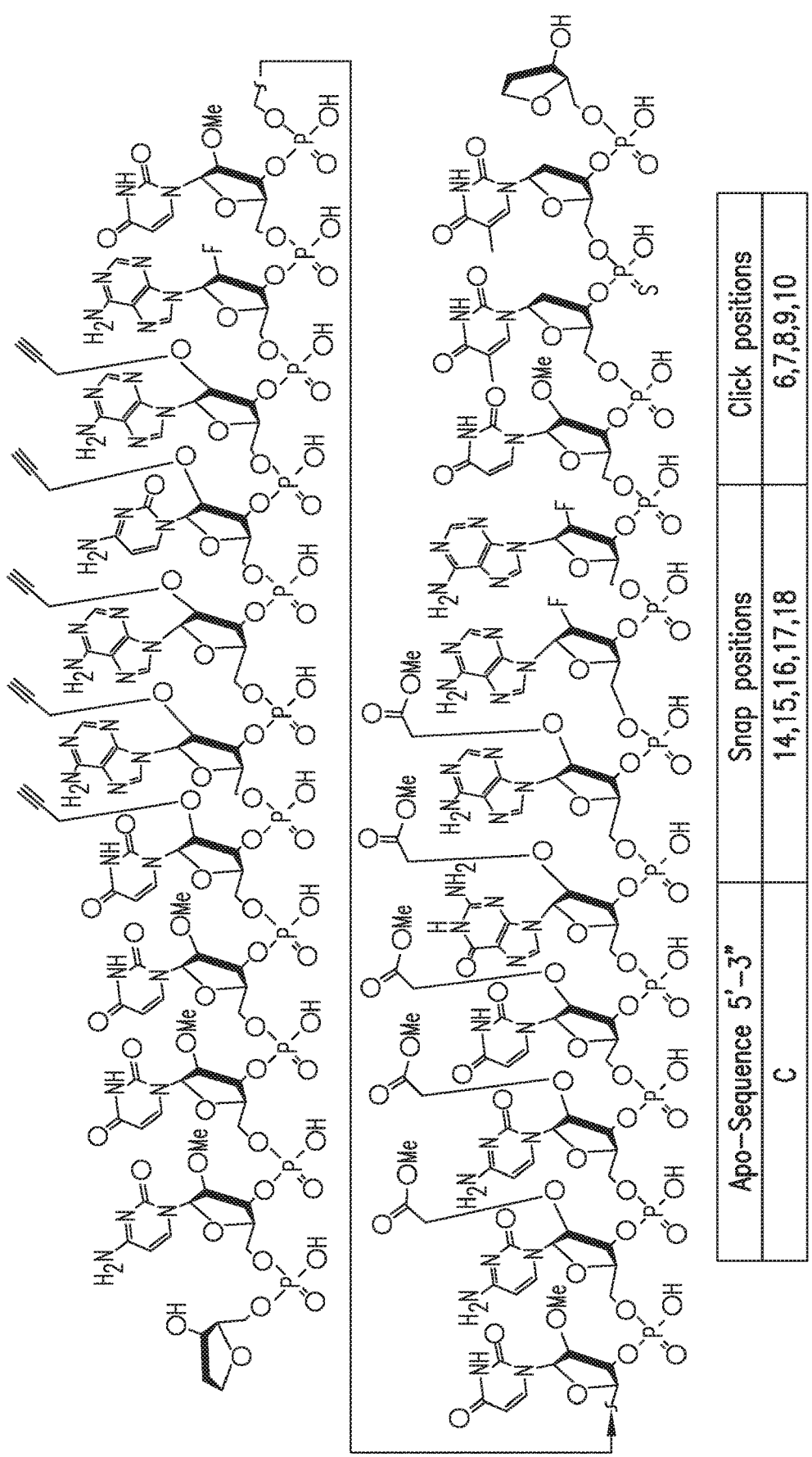
Figure 1D:
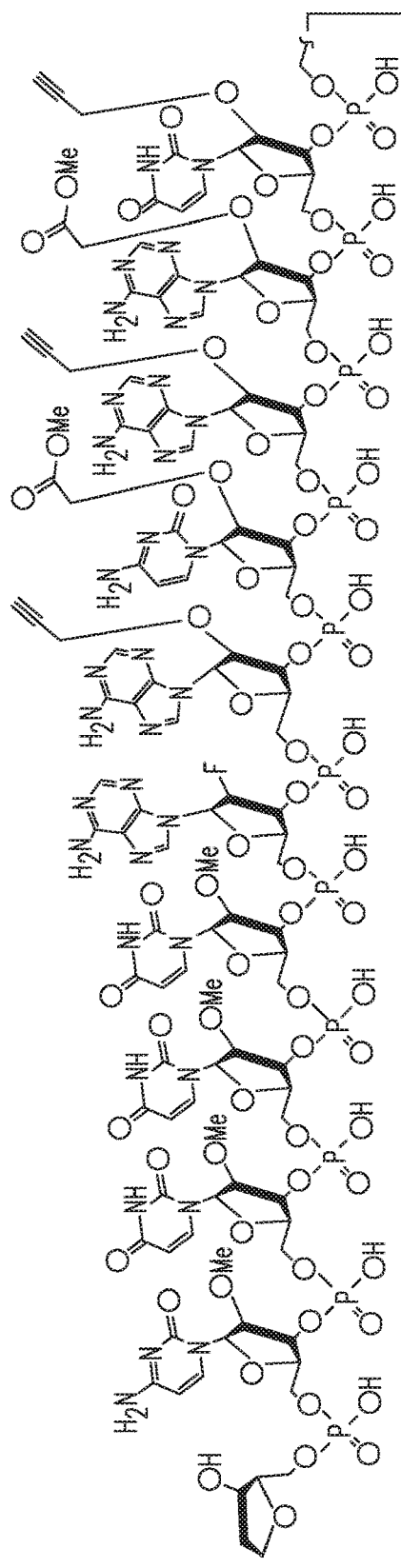
Figure 1D:
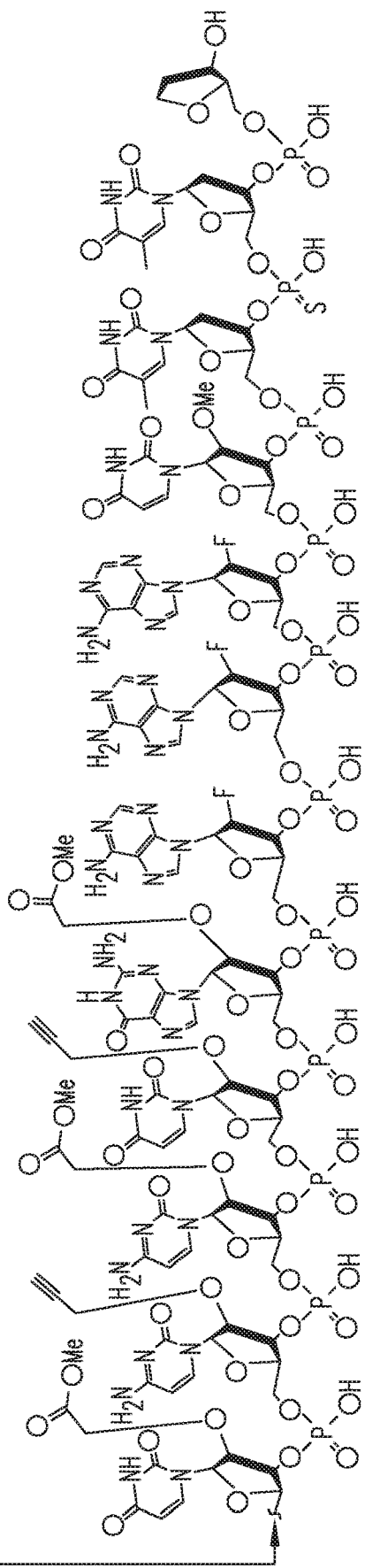

This invention relates to an orthogonal post-synthetic chemical modifications of an RNA at the 2'-position on ribose rings comprising of a "snap" or amidation step followed by a metal catalyzed Huisgen cycloaddition ("click" chemistry) step.

In one embodiment, a process for introducing two or more 2'-modifications into an RNA, wherein the RNA has an ester functional group at the 2'-position of one or more ribose rings on a strand and an alkyne functional group at the 2'-position of one or more ribose rings on the same strand, comprises: a) adding an amine to the RNA to form amides via amidation reactions with the ester functional groups; b) dissolving the modified RNA obtained in step (a) in a solvent to form a solution; and c) adding an organic azide and a metal catalyst to the solution obtained in step (b) to form triazoles via 2'-azide-alkyne cycloaddition reactions with the alkyne functional groups. The alkyne substituents at the 2'-position of the ribose rings are inert to the amidation conditions allowing for the orthogonal modification to proceed smoothly without further processing.

Using the orthogonal post-synthetic modification technique described herein, two or more positions of siRNA strands (both passenger and guide) can be independently modified to generate siRNA with desirable pharmacokinetic and pharmacodynamic properties.

The process disclosed herein provides one or more of the following benefits: 1) avoids complex, tedious multi-step syntheses of each desired modified ribonucleoside; 2) allows diverse chemical modifications using high-fidelity chemistry that is completely orthogonal to commonly used alkylamino, carboxylate and disulfide linker reactivities; 3) allows introduction of functional groups that are incompatible with modern automated solid-phase synthesis of RNA and subsequent cleavage-deprotection steps; 4) allows introduction of functional groups useful as targeting ligands; 5) enables high-throughput structure-activity relationship studies on chemically modified RNA in 96-well format; and 6) allows for orthogonal post-synthetic modifications at multiple sites of siRNA to generate a heavily modified passenger or guide RNA strand with desirable biological properties.

In one embodiment, the amidation modification and the azide-alkyne cycloaddition modification are carried out in orthogonal fashion.

In one embodiment, the process described above can be used in high-throughput format.

In one embodiment, the amidation reaction of step a) is carried out at room temperature.

In one embodiment, the amine compound in step a) is a primary amine compound. Suitable primary amine compounds include, but are not limited to, $C_{1-40}$alkylamine, amino $C_{2-10}$alcohol, allyl amine and benzyl amine, and GalNAc amine.

In another embodiment the alkylamine has other functional groups such as hydroxyl, fluoro, or cyclic hydrocarbons attached to one or more carbons on the chain.

In one embodiment, the amine compound is $C_{1-20}$alkylamine. In another embodiment, the amine compound is $C_{1-10}$alkylamine. In another embodiment, the amine compound is pentylamine.

In one embodiment, any excess amine compound in the reaction mixture from step a) is removed before step b).

In one embodiment, the ester functional group is methyl ester.

As used herein, a "snap" reaction refers to an amidation reaction between a methyl ester group at the 2'-position of an oligonucleotide ribose ring and a primary amine compound.

In another embodiment the ester group is an alky ester group with the general structure of

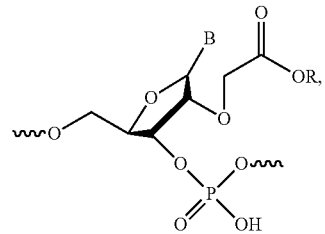

where R is $C_{1-20}$alkyl. In one embodiment, R is $C_{1-10}$alkyl. In another embodiment, R is methyl, ethyl, propyl, butyl or pentyl.

The 2'-modified RNA with amidation is further modified via click chemistry by a metal catalyzed 1,3-dipolar cycloaddition reaction between the alkyne functional group and an azide compound ("click" chemistry: Kolb, Sharpless, *Drug Discovery Today* 2003, 8, 1128).

One advantage of the presently disclosed process is that the 2'-modified RNA obtained after the amidation step can be used directly in the next step of click chemistry without further processing, thus simplifying the modification process and improving yield of product and generating heavily modified strands.

In one embodiment, the modified RNA obtained in step (a) is cleaved from its solid support using methylamine prior to being dissolved in a solvent. In another embodiment, volatiles are removed via genovac after the modified RNA is cleaved from the solid support and prior to being dissolved in a solvent.

In one embodiment, the solvent of step (b) is selected from the group consisting of an aqueous buffer solution, aqueous DMSO, aqueous $CH_3CN$, DMF, DMAc, NMP and a suitable ionic liquid. In one embodiment, the solvent is aqueous $CH_3CN$ containing 10-40% $CH_3CN$. In another embodiment, the solvent is aqueous $CH_3CN$ containing 20-30% $CH_3CN$. In yet another embodiment, the solvent is aqueous $CH_3CN$ containing 20% $CH_3CN$.

In one embodiment, the organic azide of step c) is a deprotected GalNAc azide or protected GalNac azide derivative.

As used herein, an "organic azide" means any chemical compound containing an azide functional group.

In one embodiment, the organic azide is an acyl protected GalNAc azide. In one embodiment, the organic azide is an acetyl protected GalNAc azide having the following structure:

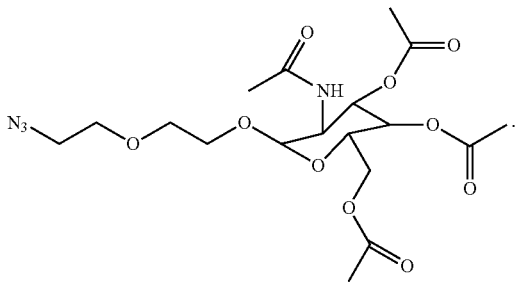 [SMILES: CC(=O)NC1C(OCCOCCN=[N+]=[N-])OC(COC(C)=O)C(OC(C)=O)C1OC(C)=O]

When acetyl protected GalNAc azide is used, de-acetylation can be carried out under basic conditions such as using methylamine or sodium carbonate after click reaction. In one embodiment, the acyl protecting groups can be removed under basic conditions prior to click reaction.

In one embodiment, the organic azide has the following structure:

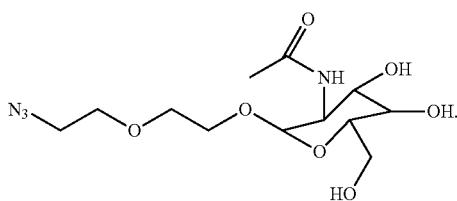 [SMILES: CC(=O)NC1C(OCCOCCN=[N+]=[N-])OC(CO)C(O)C1O]

About 10 equivalents of GalNAc azide per click site were used (total of about 50 equivalents for a 500 nmole reaction with five 2'-O-propargyl click sites).

In another embodiment, the number of equivalents of azide is up to 2 equivalents per click site.

In one embodiment, the metal catalyst in step (c) is selected from copper and ruthenium.

As used herein, a "metal catalyst" means any chemical form of copper and ruthenium, including solid-supported variants. Examples of metal catalyst include, but are not limited to, $CuBr$, $CuBr.Me_2S$, $CuI$, $CuSO_4$, $CuOAc$, $Cu(CH_3CN)_4PF_6$, $CpRuCl(PPh_3)_2$, or $Cp*RuCl(PPh_3)_2$.

In another embodiment, the metal catalyst is copper. In another embodiment, the metal catalyst is Cu(I) with a suitable ligand to stabilize the Cu(I) oxidation state. In another embodiment, the metal catalyst is CuBr. In yet another embodiment, the metal catalyst is $CuBr.SMe_2$.

In one embodiment, the step (c) reaction is performed at a temperature of between −20-200° C.

In another embodiment, the temperature is 0-120° C.
In another embodiment, the temperature is 20-100° C.
In another embodiment, the temperature is 40-60° C.
In yet another embodiment, the temperature is about 50° C.

In one embodiment, the step (c) reaction is performed at a temperature of between −20-200° C. for 0.5 to 18 h.

In another embodiment, the step (c) reaction is performed at a temperature of between 0-120° C. for 0.5 to 18 h.

In another embodiment, the step (c) reaction is performed at a temperature of between 20-100° C. for 0.5 to 18 h.

In another embodiment, the step (c) reaction is performed at a temperature of between 40-60° C. for 0.5 to 18 h.

In another embodiment, the step (c) reaction is performed at a temperature of about 50° C. for 0.5 to 18 h.

In one embodiment, the method disclosed herein can be used for attaching targeting ligands to an RNA disclosed herein.

In another embodiment, the method disclosed herein can be used for attaching targeting ligands to one or more internal nucleotides of an RNA disclosed herein.

In one embodiment, the RNA disclosed herein has an ester functional group at the 2'-position on one or more ribose rings and an alkyne functional group at the 2'-position on one or more other ribose rings.

In another embodiment, the RNA disclosed herein has an ester functional group at the 2'-position on one ribose ring and an alkyne functional group at the 2'-position on another ribose ring.

In another embodiment, the RNA disclosed herein has an ester functional group at the 2'-position on two ribose rings and an alkyne functional group at the 2'-position on two other ribose rings.

In another embodiment, the RNA disclosed herein has an ester functional group at the 2'-position on three ribose rings and an alkyne functional group at the 2'-position on three other ribose rings.

In another embodiment, the RNA disclosed herein has an ester functional group at the 2'-position on four ribose rings and an alkyne functional group at the 2'-position on four other ribose rings.

In another embodiment, the RNA disclosed herein has an ester functional group at the 2'-position on five ribose rings and an alkyne functional group at the 2'-position on five other ribose rings.

In another embodiment, the RNA disclosed herein has an ester functional group at the 2'-position on six ribose rings and an alkyne functional group at the 2'-position on six other ribose rings.

In another embodiment, the RNA disclosed herein has an ester functional group at the 2'-position on seven ribose rings and an alkyne functional group at the 2'-position on seven other ribose rings.

In another embodiment, the RNA disclosed herein has an ester functional group at the 2'-position on eight ribose rings and an alkyne functional group at the 2'-position on eight other ribose rings.

In another embodiment, the RNA disclosed herein has an ester functional group at the 2'-position on nine ribose rings and an alkyne functional group at the 2'-position on nine other ribose rings.

In another embodiment, the RNA disclosed herein has an ester functional group at the 2'-position on ten ribose rings and an alkyne functional group at the 2'-position on ten other ribose rings.

In another embodiment, the RNA disclosed herein has an ester functional group at the 2'-position on one or more ribose rings excluding the external 5' and 3' abasic rings and an alkyne functional group at the 2'-position of one or more ribose rings excluding the external 5' and 3' abasic rings.

In one embodiment, the RNA disclosed herein is an siRNA.

In one embodiment, the RNA disclosed herein is a passenger strand of a double stranded siRNA.

In one embodiment, the RNA disclosed herein is a guide strand of a double stranded siRNA.

In one embodiment, the RNA disclosed herein has up to 25 ribose rings on one strand.

In one embodiment, the RNA disclosed herein has up to 23 ribose rings on one strand.

In one embodiment, the RNA disclosed herein has up to 21 ribose rings on one strand.

In one embodiment, the RNA disclosed herein has up to 19 ribose rings on one strand.

In another embodiment, a strand comprises a combination of ribose and deoxyribose rings.

In another embodiment, the siRNA is all ribose with no abasic ring at the 3' and 5' ends.

In another embodiment, the siRNA is all ribose with no abasic rings at the end positions and no Thymidine at positions 20 and 21 from the 5' end.

In another embodiment, the siRNA comprises ribose and deoxyribose at different positions along the sequence.

In one embodiment, the RNA strand is a 21-nucleotide RNA that is homologous to an Apolipoprotein B (Apo-B) gene having a structure of A, B, C or D as shown in FIGS. 1A-1D.

In one embodiment, all ribose rings with ester functional groups at the 2'-positions are modified with amidation (snap) modifications and all ribose rings with alkyne functional groups at the 2'-positions are modified with azide-alkyne cycloaddition modifications (click).

In another embodiment, after the 2'-modifications, the 2'-modified passenger RNA strand is duplexed with a guide strand to form a double stranded RNA.

In another embodiment, the guide or passenger strand of an siRNA modified via multi-click plus multi-snap reactions can be used directly without duplexing.

In one embodiment, a process for introducing 2'-modifications into an siRNA, wherein the siRNA has a methyl ester functional group at the 2'-position on 2 ribose rings and an alkyne functional group at the 2'-position on 2 other ribose rings on the same strand, comprises: a) adding a primary amine compound to the siRNA to form amides via 2'-amidation reactions with the ester functional groups; b) generating a solution by dissolving the modified siRNA from step (a) in a solvent; and c) adding an organic azide and a metal catalyst to the solution obtained in step (b) to form triazoles via 2'-azide-alkyne cycloaddition reactions with the alkyne functional groups.

In one embodiment, a process for introducing 2'-modifications into an siRNA, wherein the siRNA has a methyl ester functional group at the 2'-position on 3 ribose rings and an alkyne functional group at the 2'-position on 3 other ribose rings on the same strand, comprises: a) adding a primary amine compound to the siRNA to form amides via 2'-amidation reactions with the ester functional groups; b) generating a solution by dissolving the modified siRNA from step (a) in a solvent; and c) adding an organic azide and a metal catalyst to the solution obtained in step (b) to form triazoles via 2'-azide-alkyne cycloaddition reactions with the alkyne functional groups.

In one embodiment, a process for introducing 2'-modifications into an siRNA, wherein the siRNA has a methyl ester functional group at the 2'-position on 4 ribose rings and an alkyne functional group at the 2'-position on 4 other ribose rings on the same strand, comprises: a) adding a primary amine compound to the siRNA to form amides via 2'-amidation reactions with the ester functional groups; b) generating a solution by dissolving the modified siRNA from step (a) in a solvent; and c) adding an organic azide and a metal catalyst to the solution obtained in step (b) to form triazoles via 2'-azide-alkyne cycloaddition reactions with the alkyne functional groups.

In one embodiment, a process for introducing 2'-modifications into an siRNA, wherein the siRNA has a methyl ester functional group at the 2'-position on 5 ribose rings and an alkyne functional group at the 2'-position on 5 other ribose rings on the same strand, comprises: a) adding a primary amine compound to the siRNA to form amides via 2'-amidation reactions with the ester functional groups; b) generating a solution by dissolving the modified siRNA from step (a) in a solvent; and c) adding an organic azide and a metal catalyst to the solution obtained in step (b) to form triazoles via 2'-azide-alkyne cycloaddition reactions with the alkyne functional groups. In one embodiment, the siRNA strand is Apo B passenger strand having a structure of A, B, C or D as shown in FIGS. 1A-1D.

In one embodiment, a process for introducing 2'-modifications into an siRNA, wherein the siRNA has a methyl ester functional group at the 2'-position on 6 ribose rings and an alkyne functional group at the 2'-position on 6 other ribose rings on the same strand, comprises: a) adding a primary amine compound to the siRNA to form amides via 2'-amidation reactions with the ester functional groups; b) generating a solution by dissolving the modified siRNA from step (a) in a solvent; and c) adding an organic azide and a metal catalyst to the solution obtained in step (b) to form triazoles via 2'-azide-alkyne cycloaddition reactions with the alkyne functional groups.

Figure 4:
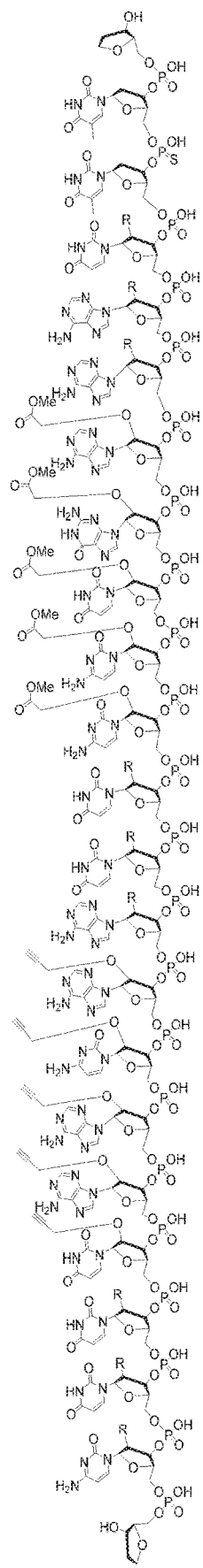
FIG. 4 is a scheme showing the structure of a starting siRNA before the reactions.

In one embodiment, the starting siRNA is a 21-nucleotide RNA that is homologous to an Apo B gene having the structure (sequence C) shown in FIG. 4.

DEFINITIONS

"2'-Modified RNA" means an RNA wherein at least one ribose ring is modified at the 2'-position.

"Alkyne functional group" means any chemical compound containing an alkyne functional group. The preferred "alkyne functional group" is the propargyl functional group.

"Ester functional group" means any chemical compound containing an ester functional group. The preferred "ester functional group" is the methyl ester or ethyl ester functional group.

"High-throughput format" means that several operations are run in parallel fashion such as for example in 96-well plate chemical synthesis, 96-well plate purification, 96-well plate chromatographic analysis and 96-well plate mass spectrometric analysis.

"Internal nucleotide" means a nucleotide in an RNA molecule that is not at the 3'- or 5'-end. For example, the internal nucleotides in a 21-nucleotide siRNA occur at positions 2-20.

"RNA" means a chemically modified or unmodified ribonucleic acid molecule (single stranded or double stranded) comprising at least 3 nucleotides, including but not limited to miRNA and siRNA. In another embodiment, "RNA" means miRNA. In another embodiment, "RNA" means siRNA. Chemical modifications include, for example, modifications to the base, ribose ring, and phosphate backbone. The base can be a canonical base (A, G, T and U) or a modified or universal base (including but not limited to inosine and nitroindole).

"Ribose ring" means the ribose moiety in a ribonucleotide.

"Targeting ligand" means a conjugate delivery moiety capable of delivering an oligonucleotide to a target cell of interest. Targeting ligands include, but are not limited to, lipids (cholesterol), sugars (NAG), proteins (transferrin),

UTILITY

The present invention provides a process for introducing chemical modifications into RNA at the 2'-position on the ribose rings. It is well known in the art that RNAs are useful for therapeutic and research purposes.

RNA SYNTHESIS

The synthesis of RNA is well known in the art.

EXAMPLES

General Working Example of "Snap Reaction"

As shown below, a primary amine compound R—NH$_2$ is added to an RNA having a methyl ester functional group at the 2'-position on the ribose ring. The reaction is carried out at room temperature resulting in an amidation reaction. Excess amine compound is removed from the reaction mixture. Reaction mixture is then used for click chemistry directly.

A suitable 2'-O-methyl ester phosphoramidite is incorporated into RNA using modern techniques based on the phosphoramidite approach. The crude, solid-support bound protected oligonucleotide is then treated with a primary amine and aged at room temperature over 1 to 4 hours. Excess amine is then washed out using DMSO, and aqueous methylamine is used to cleave the solid support and remove nucleobase and phosphate protecting groups. The crude product is then lyophilized to remove volatiles. The crude product is then purified to obtain the chemically modified RNA.

Scheme 1: Amidation of 2'-O-methyl ester group (snap reaction)

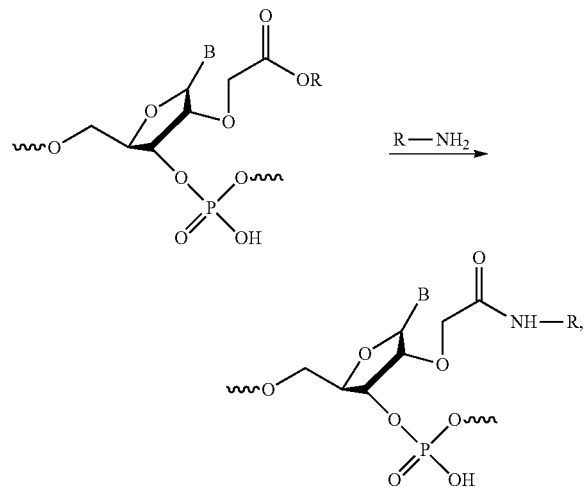

wherein B is a base selected from the group consisting of adenine (A), cytosine (C), guanine (G) or uracil (U); and R is C$_{1-40}$alkyl.

General Working Example of "Click Reaction"

A suitable 2'-O-propargyl nucleoside phosphoramidite is incorporated into RNA using modern techniques based on the phosphoramidite approach. The crude, solid-support bound protected oligonucleotide is then treated with aqueous methylamine to cleave the solid support and remove nucleobase and phosphate protecting groups. The crude product is then lyophilized to remove volatiles. The crude product is dissolved in DMSO:H$_2$O, treated with a suitable organic azide and a copper catalyst. When there are 2'-O-tert-butyldimethylsilyl protected nucleosides in the sequence the reaction mixture is treated with fluoride to remove the 2'-O-tert-butyldimethylsilyl protecting groups. The crude product is then purified to obtain the chemically modified RNA.

Scheme 2: Metal catalyzed 1,3-dipolar cycloaddition (click reaction) using 2'-O-propargyl

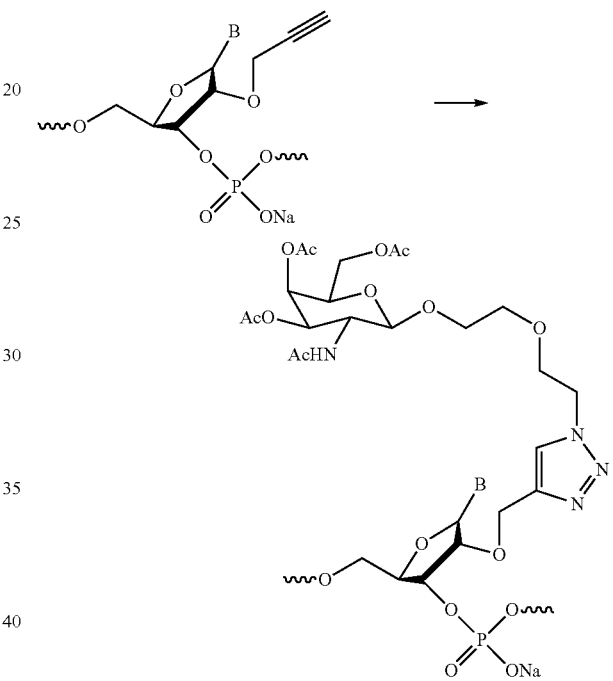

Figure 5:
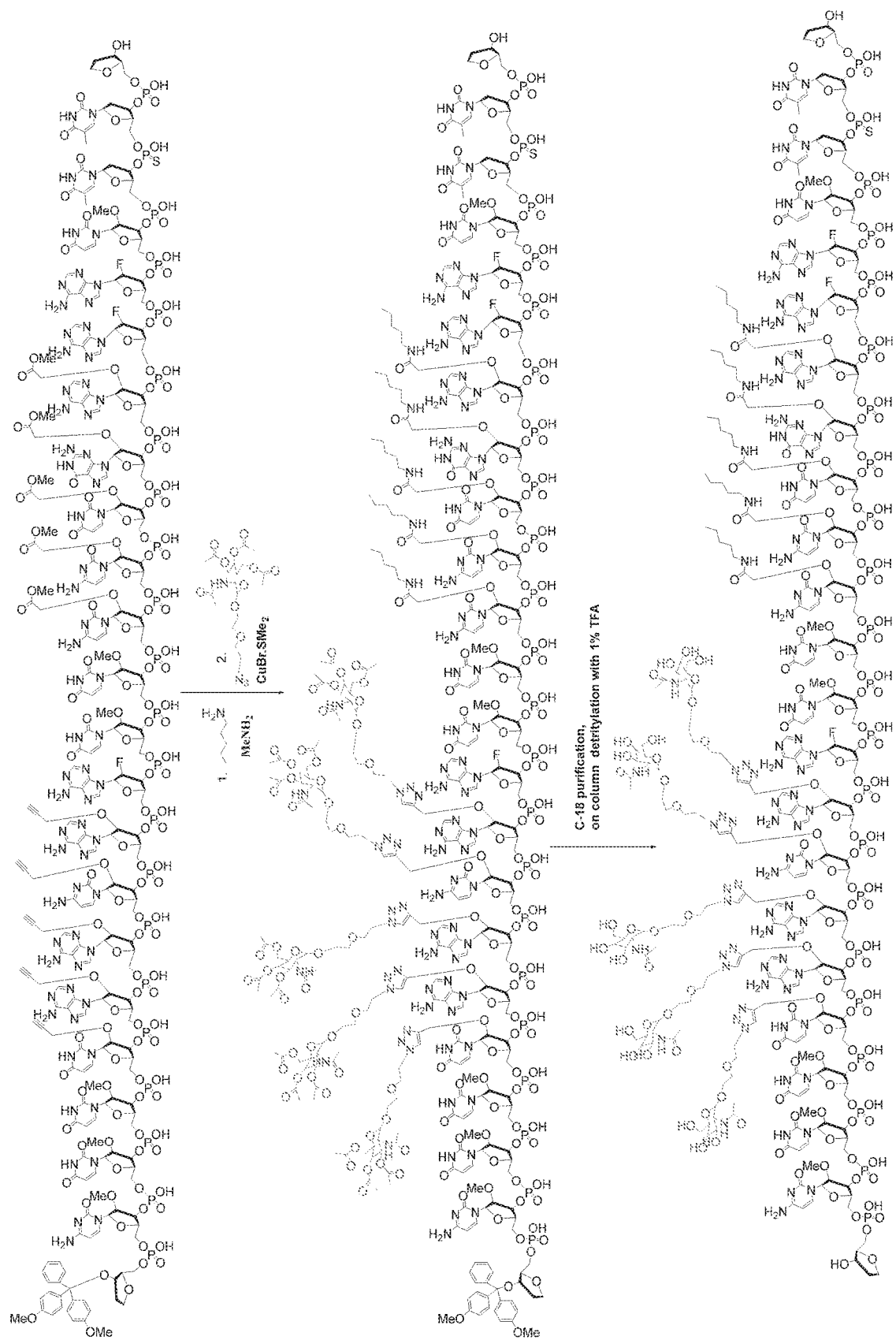
FIG. 5 is a scheme showing exemplary post-synthetic reactions with multi-snap and multi-click reactions.

Exemplary post-synthetic, multi-snap (five positions) and multi-click (five positions), reactions are shown in FIG. 5.

| Gene | Parent Passenger Strand Sequence (5'-3') |
|---|---|
| ApoB | iBCUUUAACAAUUCCUGAAAUTTiB (SEQ ID NO: 1) |

Positions 2-19 of the passenger strands were ribonucleotides, and the overhangs at positions 20 and 21 contained 2'-deoxyribonucleotide thymidines. Reverse abasic was coupled at both ends (3' and 5' positions). This unmodified siRNA was the template for systematic evaluation of modified siRNAs containing multiple modifications at selected positions along the passenger strand.

In order to examine the effect of chemical modifications for the ApoB sequence, sequences A-D (SEQ ID NOs: 2-5) were synthesized via phosphoramidite method (automated synthesis). The multi-snap and multi-click chemical modifications were then introduced into the assembled RNA by the methods described in Scheme 3.

TABLE 1

| Entry | Gene | Designed Passenger strand sequences A-D (5'-3') |
|---|---|---|
| A | ApoB | iBcCUsUUcAAsCAcAUsUCcCUsG AcAAsUTTiB (SEQ ID NO: 2) |
| B | ApoB | iBcCUcUUcAAcCAcAUsUCsCUsG AsAAsUTTiB (SEQ ID NO: 3) |
| C | ApoB | iBCUUUcAcAcCcAcAUUCsCsUsG sAsAAUTTiB (SEQ ID NO: 4) |
| D | ApoB | iBCUUUAcAsCcAsAcUsUcCsCcU GAAAUTTiB (SEQ ID NO: 5) | iB=reverse abasic, A=Adenine, C=Cytosine, G=guanine, U=uracit, T=tyamidine sA=snapped Adenine, sC=snapped Cytosine, sG=snapped guanosine, sU=snapped Uracil cA=clicked Adenine, cC=clicked Cytosine, cG=clicked guanosine, cU=clicked Uracil Protocol for Orthogonal Multi-Snap Plus Multi-Click Modifications of siRNA Step 1: Snap Procedure (5× Snap with Pentylamine):

Three hundred μL of pentylamine was slowly added to wet synthesis tips containing 500 nmol (5-6 mg) of CpG (or —C-phosphate-G-, i.e., cytosine and guanine separated by only one phosphate) bound oligonucleotide of sequence A, B, C or D (SEQ ID NOs: 2, 3, 4, or 5). The reaction mixture was aged at room temperature for over 1 hr. When reaction was done in synthesis tips, the bottom of the tips was blocked to prevent pentylamine from leaking and a vacuum was applied to remove excess pentylamine. Excess pentylamine was recycled to complete reactions.

Alternatively, the snap reactions were carried out in a vial. In one embodiment, a CPG bound oligonucleotide was transferred to a 2 mL vial and then pentylamine added to the vial containing the CPG bound oligonucleotide. When the reactions were done in a vial, the reaction mixture was filtered to remove excess pentylamine.

CPG bound oligonucleotide was treated with $MeNH_2$ (300 μL) and aged over 3 min to cleave CpG support and the $MeNH_2$ wash was collected.

CPG with DMSO (300 μL) was washed to collect any leftover material.

CPG cleaved oligonucleotide solution in $DMSO:MeNH_2$ was aged at 37° C. over 45 min to complete de-protection of nucleobase protecting groups. The mixture was cooled to 0° C. and volatiles evaporated using genovac overnight.

The multi-snap crude product was checked by LC/MS to confirm identity and used directly for multi-click reactions.

Step 2: Click Procedure:

To the lyophilized crude amidation (snap) product obtained above was added 900 μL of 20% ACN (aq.) solvent. To this mixture was added 50 μL of GalNAc azide (deacylated) followed by 50 μL of $CuBr.SMe_2$. About 10 equivalents of GaNAc azide was used per click site (total of ~50 equivalents for a 500 nmol reaction). Reaction mixture was aged in a glove box at 50° C. over 14 h with stirring.

The crude reaction mixture was checked by LC/MS to confirm identity of the product. The mixture was cooled to 0° C. and diluted with 600 μL of 1N NaCl and loaded on a C-18 purification plate and purified according to siRNA small scale purification protocol. The 5'-position of the product was de-protected (removal of dimethoxy-trityl group) on column using 1% aqueous TFA, and then collected as 5'-OH using 20% CAN (aq.). Pure material was subjected to a RP HPLC/MS to determine its molecular weight.

The C-18 purified oily product was further subjected to RP HPLC purification using the method described below. Final pure material was checked for identity using RP HPLC/MS:

Sequence A: calculated mass=9512; obtained mass=9511.
Sequence B: calculated mass=9512; obtained mass=9511.
Sequence C: calculated mass=9524; obtained mass=9523.
Sequence D: calculated mass=9512; obtained mass=9511.

Figure 2A:
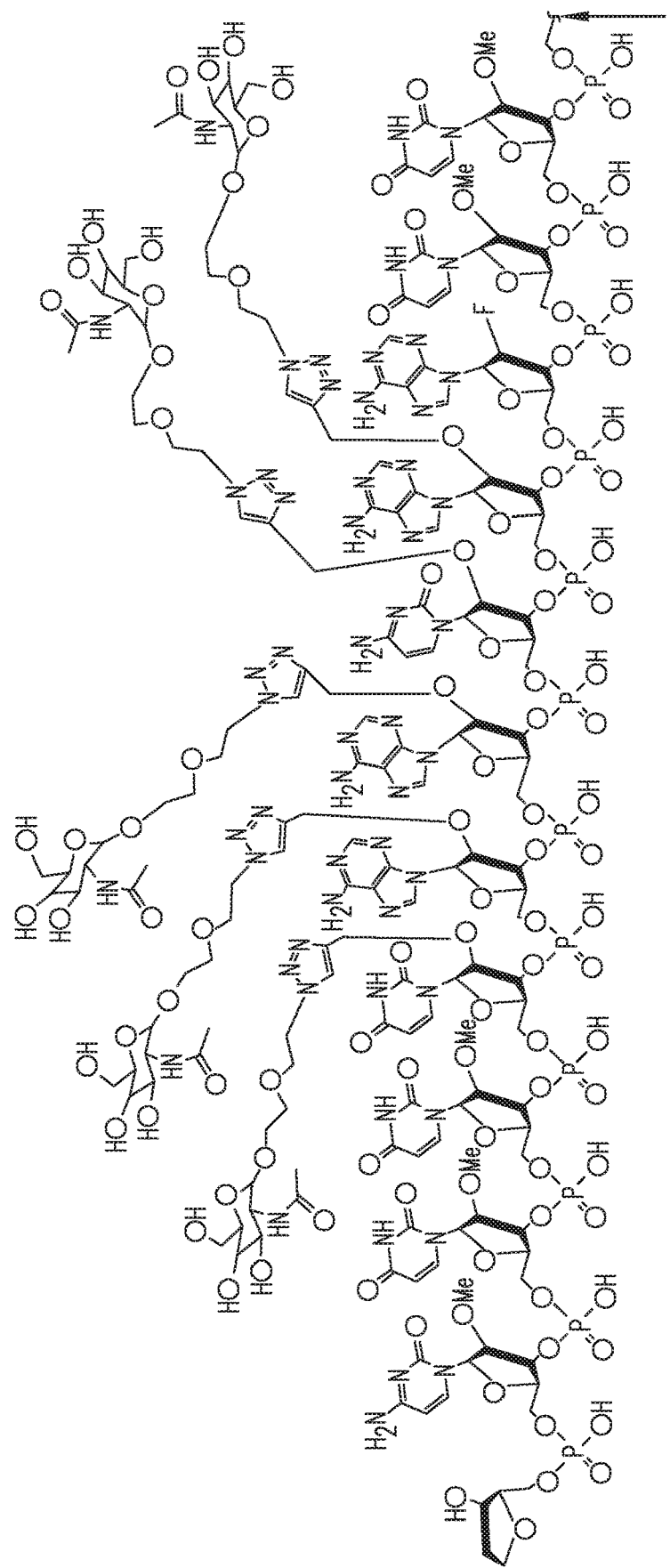
FIGS. 2A-2B show the structure of multi-snapped (with pentylamine) plus multi-clicked (GalNAc conjugates) Apo B passenger strand sequence C used in the duplex that exhibited optimal knockdown in primary hepatocyte assays.
Figure 2B:
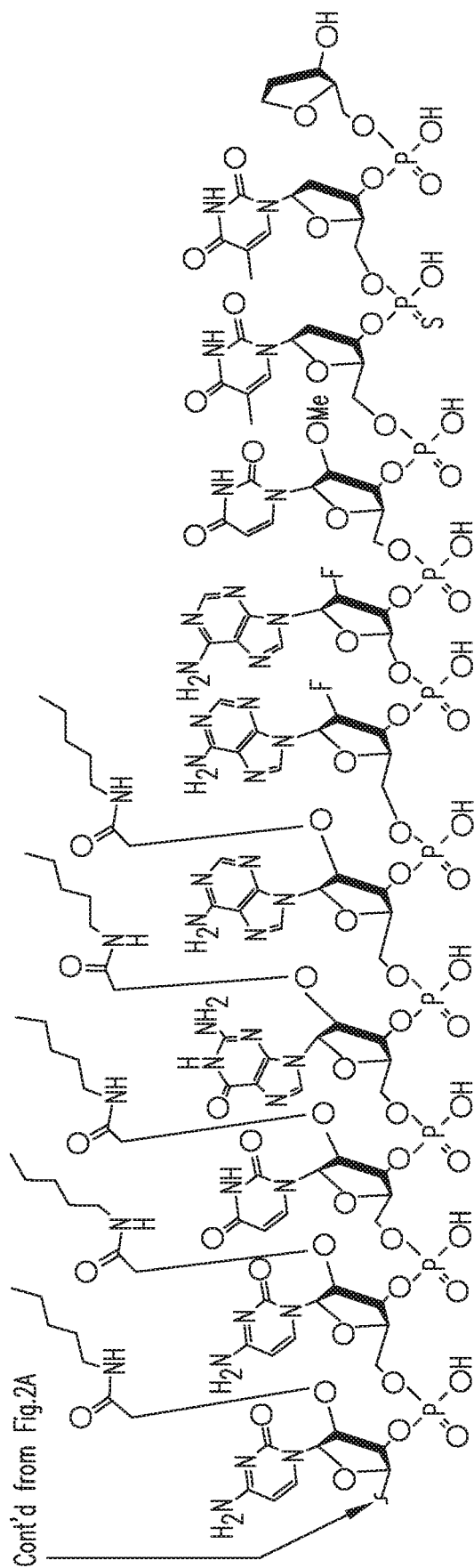

As an example, the product obtained from Sequence C after 5-snap plus 5-click reactions has a structure as shown in FIGS. 2A-2B.

This protocol can be applied in a 96-well format to generate multiple modified siRNA strands for the purpose of high throughput screening.

Recovery of Product from Automated Synthesis:

A total of 6×500 nmol scale CPG bound mononucleotide was used for each sequence. After complete automated synthesis on MerMade, isolated yield of product was ~6 mg of oligonucleotide which is ~30%.

Yield of Product from Snap and Click Combination Reactions:

Starting with ~6 mg of oligonucleotide (with methyl ester and propargyl substrates included (Sequence C=MW=7874, 0.76 μmol), theoretical yield after snap and click (MW=9514=7.2 mg). After RP HPLC purification, isolated an average of ~55 mg (~69% isolated yield)

RP HPLC/MS Method:
Mobile phase A (MPA)=HFIP (200 mM)+6.3 mM TEA;
Mobile phase B=90% MeOH+10% TFA
Column used=Aquity UPLC BEH phenyl column 1.7 μm. 2.1×50 mm.
Gradient grogram: time 0 min=10% B, 10 min=60% B; 10.01 min=100% B; 13.0 min=100% B, 13.01 min=10% B; stop time=16 min.
Flow rate=0.5 mL/min.
Injection volume=5 μL.
Detection: A260+A220. Temp=59° C.

RP HPLC Purification Method:
MPA=200 mM triethylammonium acetate (TEAA) in CAN;
MPB=200 mM TEAA in H2O.
Gradient program: Time=60 min, flow rate=10 mL/min.
Time 0 min=5% B, 5 min=12% B, 20 min=40% B, 25 min=45% B, 50 min=90% B, 52 min=100% B, 55 min=5% B. Stop time 60 min.
Injection volume=2 mL.
Temp=25° C.
Column=Phenyl X-Bridge prep Phenyl column, 5 μm, 19×50 mm, Waters.

Reagent Preparations $CuBr.SMe_2$ $CuBr.SMe_2$ (FW=205.58) used herein was prepared by dissolving 5 mg of solid into 5 mL of DMSO (0.024 mmoles/5 mL=~5 mM). About 50 μL (~0.05 mg) of CuBr.SMe2 (~243 nmol of Cu) was used for each well. The amount of Cu for each propargyl site was about 49 nmol. Considering the amount of the starting material CPG-bound monomer for the synthesis of 21 mer was 500 nmol and no isolation was done prior to the click process, the amount of Cu is approximately 10 mol % per click site.

Duplexing of 5 Snap Plus 5 Click Products (Passenger Strand) with Guide Strand (FIG. 4).

Passenger and guide strands were duplexed using SAX HPLC. HPLC absorbance A % was used to confirm ratio of passenger and guide strands is 1:1. Using SAX HPLC the following duplexes were prepared for biological assays.

SAX HPLC Method Used for Duplexing:
MPA=10 mM NaClO4,
MPB=300 mM NaClO4,
Gradient program: Time=1 min % B=5 (flow=1.3 mL/min). 4 min=50 (1.5 mL/min), 4.2 min=95 (1.2 mL/min), 4.3 min=40 (1.5 mL/min). 5.2 min=90% (1.5 mL/min), 5.6 min=10% (1.5 mL/min), 5.8 min=100% (1.5 mL/min), 6.5 min=100% (1.5 mL/min) 8 min=0%. Stop time 15 min.
Injection volumn=20 µL sample.
Temp=80° C.
Column=Dionex DNApac PA-100. 4×250 mm.

Generated Duplexes:

| Duplex Name | Amount of duplex generated |
|---|---|
| DX1 = ApoBsnapclickA | 6.3 mg |
| DX2 = ApoBsnapclickA | 5.9 mg |
| DX3 = ApoBsnapclickA | 4.6 mg |
| DX4 = ApoBsnapclickA | 4.5 mg |

Evaluating Pentylamine Snapped GalNAc Conjugates in Primary Rhesus Hepatocytes

Protocol: Cryopreserved Rhesus hepatocytes were plated using serum containing plating media on Day-1 at 40-45,000 cells/well in collagen coated 96 well plates.

Cells were allowed to attach for 15-16 hrs in the presence of serum after which the cells were washed once in serum-free maintenance media and then replaced with the cell treatment (conjugates diluted in serum-free maintenance media). Cells were incubated for 48 hrs at 37° C. and then harvested by washing with cold PBS once and lysing for 5 min on ice using PLA buffer.

ApoB Knockdown

Figure 3A:
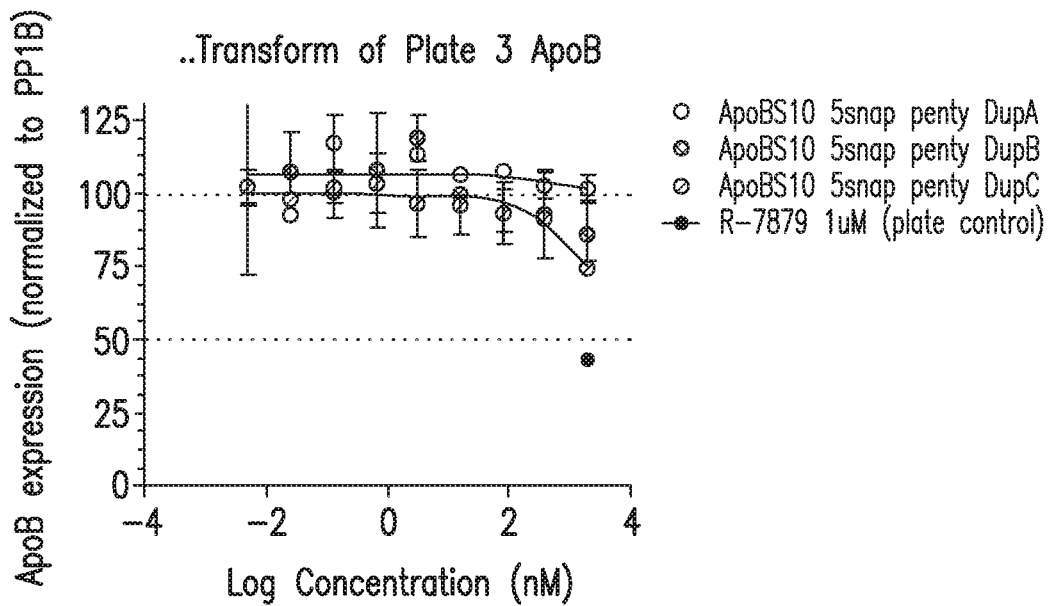
FIGS. 3A-3B show the primary hepatocyte assay results using duplexes obtained from multi-snapped (with pentylamine) and multi-clicked (GalNAc conjugates) Apo B passenger strand sequences A-D.
Figure 3B:
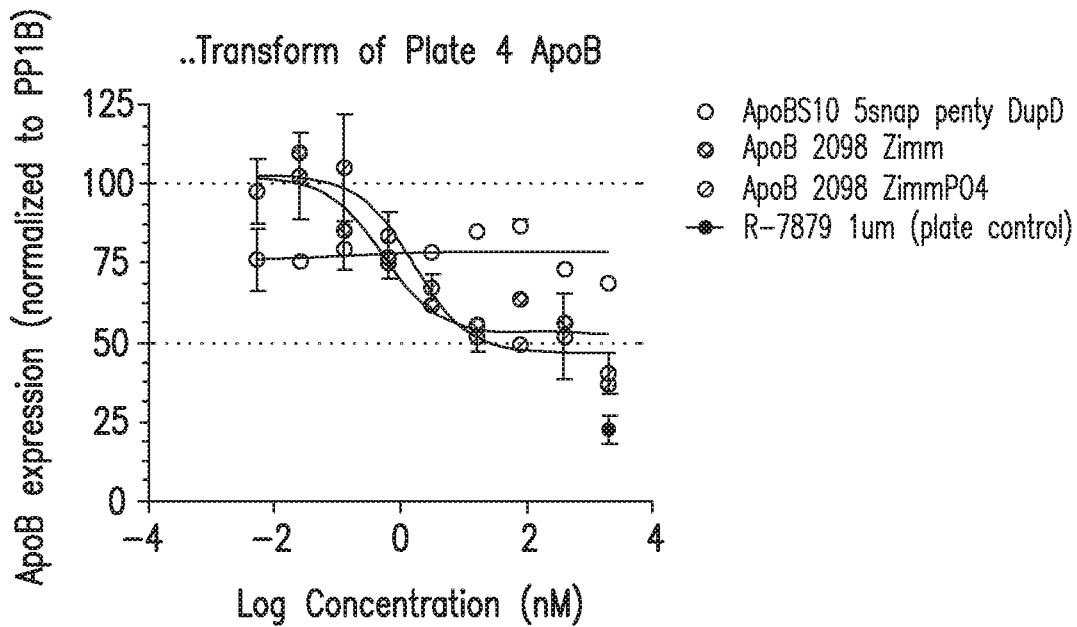

The impact on knockdown (KD) of multi-snapped plus multi-clicked chemical modifications was evaluated using primary rhesus hepatocytes of duplexes generated from multi-clicked plus multi-snapped passenger strands (A-D). The results are shown in FIGS. 3A-3B and summarized in Table 2.

TABLE 2

| Duplex ID | Description | IP (nM) | Max % KD |
|---|---|---|---|
| DX1 | ApoB(9514) Sci10 5-snap pentylamine 5-click monoGalNAc duplex A | >2000 | 0 |
| DX2 | ApoB(9514) Sci10 5-snap pentylamine 5-click monoGalNAc duplex B | >2000 | 0 |
| DX3 | ApoB(9514) Sci10 5-snap pentylamine 5-click monoGalNAc duplex C | 38.5 | 61 |
| DX4 | ApoB(9514) Sci10 5-snap pentylamine 5-click monoGalNAc duplex D | >2000 | 22 |

As can be seen from Table 2, the optimal knockdown was observed for the duplex obtained from multi-snapped (5 positions) and multi-clicked (5 positions) passenger sequence C (SEQ ID NO: 4).

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

What is claimed is:

1. A process for introducing two or more 2'-modifications into an RNA, wherein the RNA has a 2'-O substituent containing an alkyl ester functional group at the 2'-position on one or more ribose rings of a strand and a 2'-O substituent containing an alkyne functional group at the 2'-position on one or more ribose rings on the same strand, comprising: a) adding an amine compound to the RNA to form amidation reaction products with the alkyl ester functional groups; b) dissolving the modified RNA from step (a) in a solvent to form a solution; and c) adding an organic azide and a copper or ruthenium catalyst to the solution obtained in step (b) to form 2'-azide-alkyne cycloaddition reaction products with the alkyne functional groups.

2. The process of claim 1, further comprising:
   prior to step (a), preparing the RNA from solid-phase synthesis, thereby attaching the RNA to a solid support; and cleaving the modified RNA from step (a) from its solid support with methylamine, prior to being dissolved in the solvent in step (b).

3. The process of claim 1, wherein the alkyl ester functional group is methyl ester.

4. The process of claim 1, wherein the amine compound in step a) is a primary amine.

5. The process of claim 4, wherein the amine compound is pentylamine.

6. The process of claim 1, wherein the reaction in step a) is carried out at room temperature.

7. The process of claim 1, wherein the organic azide of step c) is GalNAc azide or a protected GalNAc azide.

8. The process of claim 7, wherein the organic azide is acylated GalNAc azide, and wherein the process further comprises deacylation after the cycloaddition reaction is complete to remove the acyl protecting groups.

9. The process of claim 1, wherein the solvent of step (b) is aqueous $CH_3CN$ containing 20% $CH_3CN$.

10. The process of claim 1, wherein the copper catalyst of step (c) is Cu(I) with a suitable ligand to stabilize the Cu(I) oxidation state.

11. The process of claim 1, wherein step (c) is performed at a temperature of between 20° C. to 100° C. for 0.5 to 18 hours.

12. The process of claim 1, wherein the RNA has a 2'-O substituent containing an alkyl ester functional group at the 2'-position on 5 ribose rings and a 2'-O substituent containing an alkyne functional group at the 2'-position on 5 other ribose rings on the same strand.

13. The process of claim 12, wherein the 5 ribose rings with the alkyl ester functional groups are modified with amidation reactions and the 5 ribose rings with the alkyne functional groups are modified with azide-alkyne cycloaddition reactions.

14. The process of claim 13, wherein the RNA is an Apo B passenger strand having a sequence of A, B, C or D (SEQ ID NOs: 2, 3, 4, or 5).

15. The process of claim 14, wherein the RNA is an Apo B passenger strand having a sequence of C (SEQ ID NO: 4).

16. The process of claim 14, further comprising, after the 2'-modifications, duplexing the modified passenger strand with a guide strand to form a double stranded RNA.

17. A process for introducing 2'-modifications into an siRNA, wherein the siRNA has a 2'-O substituent containing a methyl ester functional group at the 2'-position on 5 ribose rings on a strand and a 2'-O substituent containing an alkyne functional group at the 2'-position on 5 other ribose rings on the same strand, comprising: a) adding a primary amine compound to the siRNA to form amides via 2'-amidation reactions with all ester functional groups; b) dissolving the modified siRNA from step (a) in a solvent to form a solution; and c) adding an organic azide and a copper or ruthenium catalyst to the solution obtained in the previous step to form triazoles via 2'-azide-alkyne cycloaddition reactions with all alkyne functional groups.

18. The process of claim 17, further comprising:
prior to step (a), preparing the siRNA from solid-phase synthesis, thereby attaching the siRNA to a solid support; and
cleaving the modified siRNA from step (a) from its solid support with methylamine, prior to being dissolved in the solvent in step (b).

19. The process of claim 1, wherein the alkyl ester functional group of the RNA has the structure of

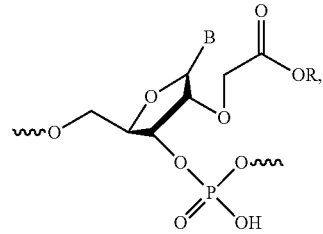

wherein R is $C_{1-20}$ alkyl, and B is a nucleobase.

* * * * *

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: reverse abasic cap
<220> FEATURE:
<221> NAME/KEY: misc_feature
<222> LOCATION: (20)..(20)
<223> OTHER INFORMATION: 2'-deoxy thymidine
<220> FEATURE:
<221> NAME/KEY: misc_feature
<222> LOCATION: (21)..(21)
<223> OTHER INFORMATION: 2'-deoxy thymidine
<220> FEATURE:
<221> NAME/KEY: misc_feature
<222> LOCATION: (21)..(21)
<223> OTHER INFORMATION: reverse abasic cap

<400> SEQUENCE: 1
cuuuaacaau uccugaaaut t                                             21
```

```
<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: reverse abasic cap
<220> FEATURE:
<221> NAME/KEY: misc_feature
<222> LOCATION: (1)..(1)
<223> OTHER INFORMATION: click modification: 2'-azide-cycloaddition
      reaction modified.
<220> FEATURE:
<221> NAME/KEY: misc_feature
<222> LOCATION: (3)..(3)
<223> OTHER INFORMATION: snap modification: 2'-amidation reaction
      modified.
<220> FEATURE:
<221> NAME/KEY: misc_feature
<222> LOCATION: (5)..(5)
<223> OTHER INFORMATION: click modification: 2'-azide-cycloaddition
      reaction modified.
<220> FEATURE:
<221> NAME/KEY: misc_feature
<222> LOCATION: (7)..(7)
<223> OTHER INFORMATION: snap modification: 2'-amidation reaction
      modified.
<220> FEATURE:
<221> NAME/KEY: misc_feature
<222> LOCATION: (9)..(9)
<223> OTHER INFORMATION: click modification: 2'-azide-cycloaddition
      reaction modified.
<220> FEATURE:
<221> NAME/KEY: misc_feature
<222> LOCATION: (11)..(11)
<223> OTHER INFORMATION: snap modification: 2'-amidation reaction
      modified.
<220> FEATURE:
<221> NAME/KEY: misc_feature
<222> LOCATION: (13)..(13)
<223> OTHER INFORMATION: click modification: 2'-azide-cycloaddition
      reaction modified.
<220> FEATURE:
<221> NAME/KEY: misc_feature
<222> LOCATION: (15)..(15)
<223> OTHER INFORMATION: snap modification: 2'-amidation reaction
      modified.
<220> FEATURE:
<221> NAME/KEY: misc_feature
<222> LOCATION: (17)..(17)
<223> OTHER INFORMATION: click modification: 2'-azide-cycloaddition
      reaction modified.
<220> FEATURE:
<221> NAME/KEY: misc_feature
<222> LOCATION: (19)..(19)
<223> OTHER INFORMATION: snap modification: 2'-amidation reaction
      modified.

<400> SEQUENCE: 2
cuuuaacaau uccugaaaut t                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: reverse abasic cap
<220> FEATURE:
<221> NAME/KEY: misc_feature
<222> LOCATION: (1)..(1)
<223> OTHER INFORMATION: click modification: 2'-azide-cycloaddition
      reaction modified.
<220> FEATURE:
<221> NAME/KEY: misc_feature
<222> LOCATION: (3)..(3)
<223> OTHER INFORMATION: click modification: 2'-azide-cycloaddition
      reaction modified.
<220> FEATURE:
<221> NAME/KEY: misc_feature
<222> LOCATION: (5)..(5)
<223> OTHER INFORMATION: click modification: 2'-azide-cycloaddition
      reaction modified.
<220> FEATURE:
<221> NAME/KEY: misc_feature
<222> LOCATION: (7)..(7)
<223> OTHER INFORMATION: click modification: 2'-azide-cycloaddition
      reaction modified.
<220> FEATURE:
<221> NAME/KEY: misc_feature
<222> LOCATION: (9)..(9)
<223> OTHER INFORMATION: click modification: 2'-azide-cycloaddition
      reaction modified.
<220> FEATURE:
<221> NAME/KEY: misc_feature
<222> LOCATION: (11)..(11)
<223> OTHER INFORMATION: snap modification: 2'-amidation reaction
      modified.
<220> FEATURE:
<221> NAME/KEY: misc_feature
<222> LOCATION: (13)..(13)
<223> OTHER INFORMATION: snap modification: 2'-amidation reaction
      modified.
<220> FEATURE:
<221> NAME/KEY: misc_feature
<222> LOCATION: (15)..(15)
<223> OTHER INFORMATION: snap modification: 2'-amidation reaction
      modified.
<220> FEATURE:
<221> NAME/KEY: misc_feature
<222> LOCATION: (17)..(17)
<223> OTHER INFORMATION: snap modification: 2'-amidation reaction
      modified.
<220> FEATURE:
<221> NAME/KEY: misc_feature
<222> LOCATION: (19)..(19)
<223> OTHER INFORMATION: snap modification: 2'-amidation reaction
      modified.
<220> FEATURE:
<221> NAME/KEY: misc_feature
<222> LOCATION: (21)..(21)
<223> OTHER INFORMATION: reverse abasic cap

<400> SEQUENCE: 3
cuuuaacaau uccugaaaut t                                            21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: reverse abasic cap
<220> FEATURE:
<221> NAME/KEY: misc_feature
<222> LOCATION: (5)..(5)
<223> OTHER INFORMATION: click modification: 2'-azide-cycloaddition
      reaction modified.
<220> FEATURE:
<221> NAME/KEY: misc_feature
<222> LOCATION: (6)..(6)
<223> OTHER INFORMATION: click modification: 2'-azide-cycloaddition
      reaction modified.
<220> FEATURE:
<221> NAME/KEY: misc_feature
<222> LOCATION: (7)..(7)
<223> OTHER INFORMATION: click modification: 2'-azide-cycloaddition
      reaction modified.
<220> FEATURE:
<221> NAME/KEY: misc_feature
<222> LOCATION: (8)..(8)
<223> OTHER INFORMATION: click modification: 2'-azide-cycloaddition
      reaction modified.
<220> FEATURE:
<221> NAME/KEY: misc_feature
<222> LOCATION: (9)..(9)
<223> OTHER INFORMATION: click modification: 2'-azide-cycloaddition
      reaction modified.
<220> FEATURE:
<221> NAME/KEY: misc_feature
<222> LOCATION: (13)..(13)
<223> OTHER INFORMATION: snap modification: 2'-amidation reaction
      modified.
<220> FEATURE:
<221> NAME/KEY: misc_feature
<222> LOCATION: (14)..(14)
<223> OTHER INFORMATION: snap modification: 2'-amidation reaction
      modified.
<220> FEATURE:
<221> NAME/KEY: misc_feature
<222> LOCATION: (15)..(15)
<223> OTHER INFORMATION: snap modification: 2'-amidation reaction
      modified.
<220> FEATURE:
<221> NAME/KEY: misc_feature
<222> LOCATION: (16)..(16)
<223> OTHER INFORMATION: snap modification: 2'-amidation reaction
      modified.
<220> FEATURE:
<221> NAME/KEY: misc_feature
<222> LOCATION: (17)..(17)
<223> OTHER INFORMATION: snap modification: 2'-amidation reaction
      modified.
<220> FEATURE:
<221> NAME/KEY: misc_feature
<222> LOCATION: (21)..(21)
<223> OTHER INFORMATION: reverse abasic cap

<400> SEQUENCE: 4
cuuuaacaau uccugaaaut t                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(21)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: reverse abasic cap
<220> FEATURE:
<221> NAME/KEY: misc_feature
<222> LOCATION: (6)..(6)
<223> OTHER INFORMATION: click modification: 2'-azide-cycloaddition
      reaction modified.
<220> FEATURE:
<221> NAME/KEY: misc_feature
<222> LOCATION: (7)..(7)
<223> OTHER INFORMATION: snap modification: 2'-amidation reaction
      modified.
<220> FEATURE:
<221> NAME/KEY: misc_feature
<222> LOCATION: (8)..(8)
<223> OTHER INFORMATION: click modification: 2'-azide-cycloaddition
      reaction modified.
<220> FEATURE:
<221> NAME/KEY: misc_feature
<222> LOCATION: (9)..(9)
<223> OTHER INFORMATION: snap modification: 2'-amidation reaction
      modified.
<220> FEATURE:
<221> NAME/KEY: misc_feature
<222> LOCATION: (10)..(10)
<223> OTHER INFORMATION: click modification: 2'-azide-cycloaddition
      reaction modified.
<220> FEATURE:
<221> NAME/KEY: misc_feature
<222> LOCATION: (11)..(11)
<223> OTHER INFORMATION: snap modification: 2'-amidation reaction
      modified.
<220> FEATURE:
<221> NAME/KEY: misc_feature
<222> LOCATION: (12)..(12)
<223> OTHER INFORMATION: click modification: 2'-azide-cycloaddition
      reaction modified.
<220> FEATURE:
<221> NAME/KEY: misc_feature
<222> LOCATION: (13)..(13)
<223> OTHER INFORMATION: snap modification: 2'-amidation reaction
      modified.
<220> FEATURE:
<221> NAME/KEY: misc_feature
<222> LOCATION: (14)..(14)
<223> OTHER INFORMATION: click modification: 2'-azide-cycloaddition
      reaction modified.
<220> FEATURE:
<221> NAME/KEY: misc_feature
<222> LOCATION: (15)..(15)
<223> OTHER INFORMATION: snap modification: 2'-amidation reaction
      modified.
<220> FEATURE:
<221> NAME/KEY: misc_feature
<222> LOCATION: (21)..(21)
<223> OTHER INFORMATION: reverse abasic cap

<400> SEQUENCE: 5
cuuuaacaau uccugaaaut t                                           21
```